United States Patent [19]
Sasa et al.

[11] Patent Number: 4,765,312
[45] Date of Patent: Aug. 23, 1988

[54] ENDOSCOPE

[75] Inventors: Hiroyuki Sasa; Akira Suzuki, both of Tokyo, Japan

[73] Assignee: Olympus Optical Co., Ltd., Japan

[21] Appl. No.: 79,140

[22] Filed: Jul. 29, 1987

[30] Foreign Application Priority Data

Jul. 30, 1986 [JP] Japan ................................. 61-179158

[51] Int. Cl.⁴ ............................................... A61B 1/00
[52] U.S. Cl. ........................................................ 128/4
[58] Field of Search ........................................ 128/4, 6

[56] References Cited

U.S. PATENT DOCUMENTS

| | | | |
|---|---|---|---|
| 4,261,343 | 4/1981 | Ouchi et al. | 128/4 |
| 4,538,593 | 9/1985 | Ishii | 128/4 |
| 4,566,437 | 1/1986 | Yamaguchi | 128/4 |
| 4,668,226 | 5/1987 | Omata et al. | 128/4 X |

*Primary Examiner*—William H. Grieb

[57] ABSTRACT

An endoscope includes a connecting assembly for connecting a syringe, for supplying a supplementary fluid to an orifice, formed on a distal end portion of an insertion portion. The connecting assembly comprises a hollow mount member which is formed to extend from a periphery portion of an opening formed on a housing of the operation portion of the endoscope, and a shoulder is formed on the outer peripheral surface. In addition, a block, having a cavity, an inlet, and an outlet for serially connecting the cavity in a fluid supply path extended to the orifice, is received in the housing. A distal end of the mount piece on which the syringe can be mounted is inserted into the cavity of the block via the mount member. A locking member having an arm is mounted on the mount member by causing the arm to be abutted on the inner side of the shoulder. The mount piece is securely retained inside the mount member by threadably fixing a support member to the locking member.

8 Claims, 7 Drawing Sheets

ENDOSCOPE

BACKGROUND OF THE INVENTION

The present invention relates to an endoscope, which includes an insertion portion to be inserted in a body cavity, and an operation portion for the folding and controlling thereof, having a connecting means for connecting a supplementary liquid injection means at the operation portion.

In one conventional endoscope, the distal end of a nozzle is directed toward an observation window, formed on the distal end of a portion for insertion into a body cavity, so as to clean the observation window by spraying it with cleaning water supplied through the nozzle from a water-supply pipe path extending inside the endoscope. In this way, any mucus or contaminant attached to the observation window can be easily removed. However, when this cleaning method is employed, the cleaning water cannot be sprayed at high pressure, and hence the observation window cannot be cleaned to the degree desired.

Japanese Patent Disclosure (Kokai) No. 58-175542 discloses an endoscope having a supplementary injection unit which communicates with a water-supply pipe path extending inside the endoscope. This supplementary injection unit includes a connecting means for connecting a high-pressure air injection means, such as a syringe, at the operation portion of the endoscope. This connecting means communicates with the supply pipe path which extends to a nozzle inside the endoscope. The injection means is connected to the connecting means, so as to supply high-pressure cleaning water to the nozzle, thereby to clean the observation window thoroughly.

The connecting means of the supplementary injection unit has a syringe mounting piece mounted in a watertight fashion on the operation portion. The syringe mounting piece is fitted in a supporting cylinder and is inserted into a metal sleeve formed on a cover of the operation portion, and then pressed towards the inside of the operation portion by a fastening ring which is fastened to the metal sleeve on the supporting cylinder.

The above sleeve is made of a metal such as stainless steel, in order for it to have sufficient strength for supporting the fastening ring. In order to maintain the strength of the connection between the sleeve and the cover, these two parts must be connected not by simple adhesion, but by a high-strength method such as brazing. Therefore, the cover must be made of the same type of metal as the sleeve.

Nowadays, RF current treatment is very frequently performed by means of an endoscope. When RF current treatment is performed using the conventional endoscope, since the cover and the sleeve are made of metal, part of the RF current may leak through the cover and sleeve, thereby giving rise to the risk of injury to the operator (such as a doctor) through electric shock.

In order to prevent such a leakage of current, an endoscope has been proposed wherein the cover and sleeve are coated with a resist.

However, when the cover and sleeve are coated with a resist, part of the underlying metal surface may become exposed by paint peeling, damage, and the like, with the result that current may flow through this metal surface.

SUMMARY OF THE INVENTION

It is an object of the present invention to solve the above-mentioned problems associated with the conventional endoscope.

It is another object of the present invention to provide an endoscope having a connecting means which do not require the use of a cumbersome assembly operation such as brazing.

It is still another object of the present invention to provide an endoscope having a connecting means which can be easily assembled, while being able to retain sufficient connection strength between itself and the mount piece.

It is yet another object of the present invention to provide an endoscope having a connecting means made up of components which can be assembled easily and reliably, and which, following assembly, will not become displaced from their respective positions.

It is a further object of the present invention to provide an endoscope which can be used for RF treatment or the like, without any danger of the operator receiving an electric shock, and which is light weight and easy to handle.

In order to achieve the above objects, the connecting means of an endoscope according to the present invention comprises a hollow mount member, which includes shoulder means formed on the outer peripheral surface and which is formed to extend from a periphery portion of an opening formed in a housing of an operation portion; a block which is received in the housing, the block having a cavity facing the opening, and an inlet and outlet for enabling that portion of the block which contains the cavity to be inserted hydraulically into a supply pipe; a mount piece, which is inserted from the extended end of the mount member, such that its distal end portion is placed in the cavity, and on which a supplementary fluid injection means is mounted; a seal member for forming a seal between the mount piece and the periphery portion of the cavity; a locking member having an arm abutting on the side of the shoulder means which faces the housing; and a support member for supporting the mount piece, which is threadably fixed to the locking member to press the mount member, whereby the shoulder means is clamped between the support member and the arm.

According to an embodiment of the present invention, a sleeve is mounted on the distal end of the mount piece, to thereby form a check valve, and the mount piece and sleeve are fitted in a supporting cylinder mounted in the mount member. The supporting cylinder is sealed against the inner surface of the mount member, and is preferably sealed against the opening face of the block, by means of the seal member.

In addition, a pair of locking pieces are formed so as to oppose each other on the inner end of the cylinder, and the cavity of the block is formed so that it has a rectangular cross section. It is preferable that the locking pieces are engaged with the side wall of the cavity, in order to permit the block to move axially, relative to the housing, while preventing such movement in the circumferential direction.

A flange is formed on an intermediate portion of the mount piece, along the axial direction thereof, so as to extend radially outwardly. The flange is preferably clamped between the supporting cylinder and the support member.

The mount member has a pair of projections formed on opposite positions of its outer end portion, and the supporting cylinder has a pair of projections formed at positions matching with the projections of the mount means. The flange of the mount piece preferably has notches in which the respective projections of the mount means and the supporting cylinder can be fitted.

The housing is made of an insulating material and can include an insulating cap for covering the locking member, the supporting member, and the mount piece.

Other characteristics and advantages of the present invention will be apparent from the following description, taken with reference to the accompanying drawings.

DETAILED DESCRIPTION OF THE PREFERRED EMBODIMENT

Figure 1:
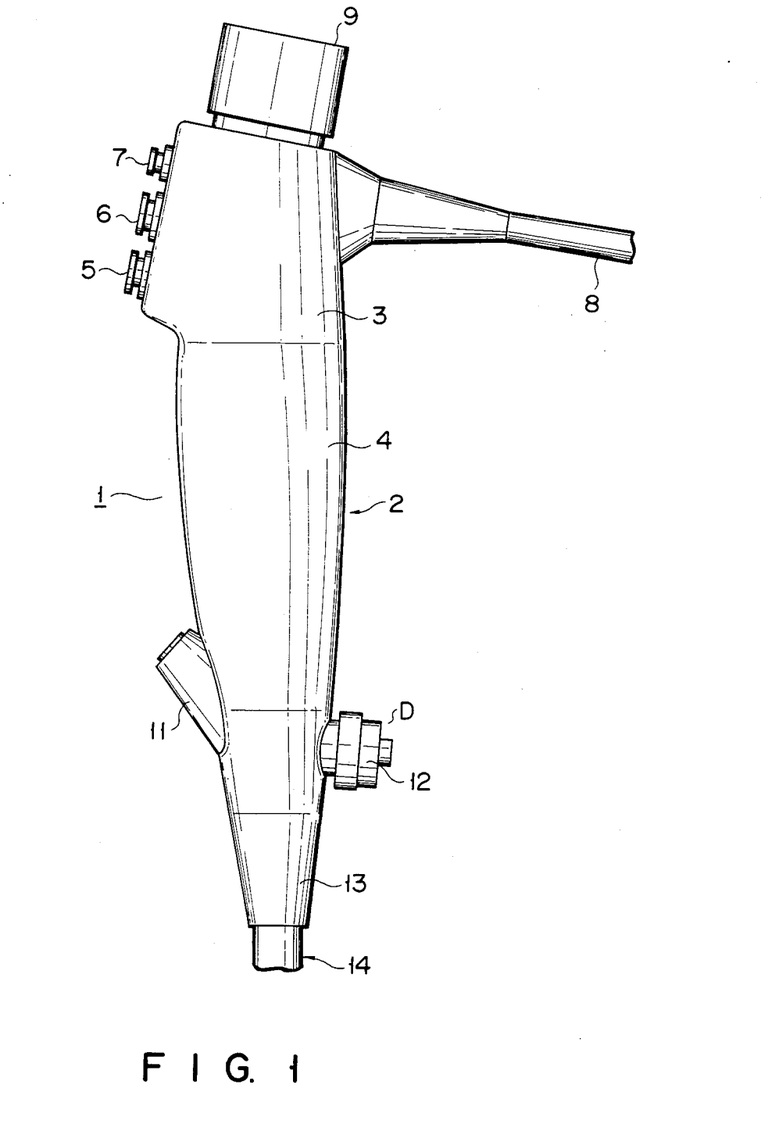
FIG. 1 is a schematic view illustrating an operation portion of an endoscope according to an embodiment of the present invention.

As shown in FIG. 1, endoscope 1 comprises operation portion 2 for operating this endoscope. Operation portion 2 is constituted by control portion 3 and grip portion 4. Air-/liquid-supply switching operation valve 5, suction operation valve 6, and gas operation valve 7 are disposed on one side of control portion 3. Universal cord 8 for light guide extends from control portion 3, and eyepiece 9 is arranged on the outer end portion thereof. Insertion opening 11 is provided on a side surface of grip portion 4, and a connecting assembly or means 12 for connecting a supplementary injection means such as a syringe is provided on the other side surface thereof opposite to insertion opening 11. Insertion portion 14 to be inserted into a body cavity is connected to the other end portion of grip portion 4 opposite to control portion 3 via connecting cylinder 13.

Figure 2:
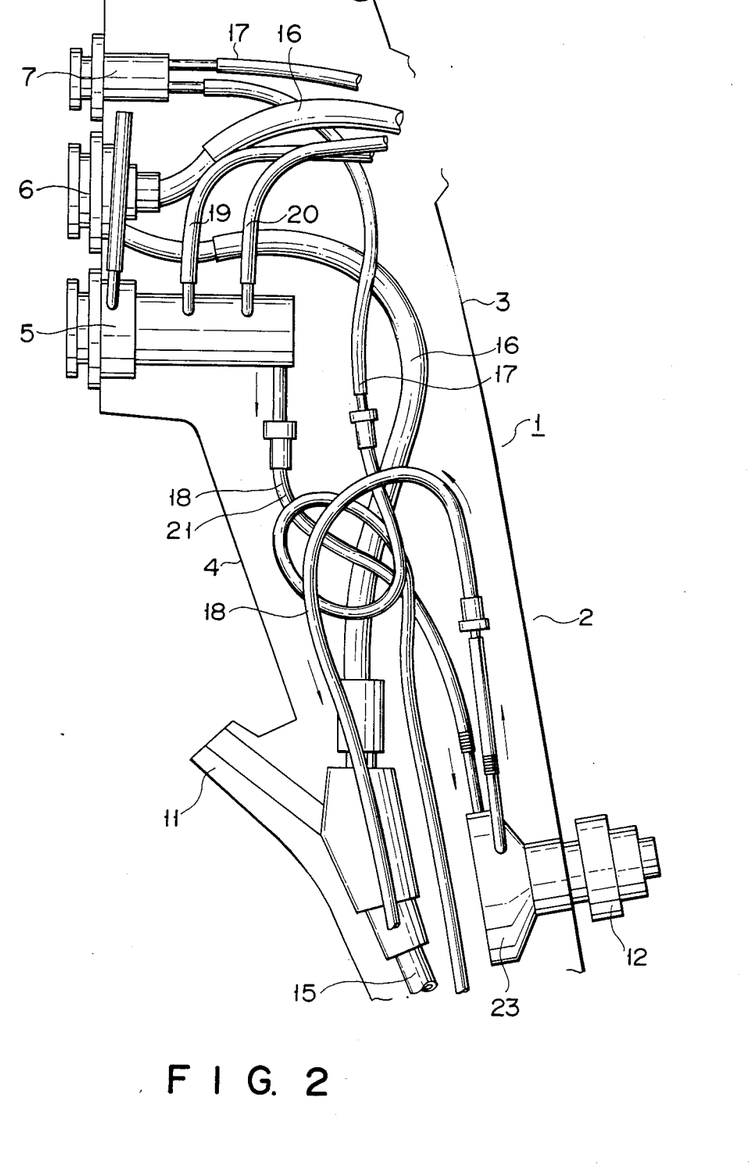
FIG. 2 is a schematic view illustrating an inner structure of the operation portion of the endoscope in FIG. 1.

As shown in FIG. 2, tube 15 constituting a channel for inserting a treatment tool is provided inside of each of operation portion 2 and insertion portion 14. The proximal end of tube 15 is connected to insertion portion 11. The treatment tool introduced from insertion opening 11 is guided to the inside of channel 15 to extend into the body cavity from the distal end of insertion portion 14.

Suction tube 16 is connected to a portion midway along channel 15. Tube 16 is guided from the inside of operation portion 2 to the inside of universal cord 8, and connected to a suction source not shown. Suction operation valve 6 is inserted into a portion midway along suction tube 16, and suction tube 16 is opened and closed by suction operation valve 6 so as to control a suction operation.

Furthermore, gas-supply tube 17 is inserted into operation portion 2, universal cord 8, and insertion portion 14, and one end portion of tube 17 is connected to a gas cylinder (not shown). Gas operation valve 7 is inserted into a portion midway along tube 17 in the same manner as described above. A path formed in tube 17 is opened and closed by operating gas operation valve 7 so as to control supply of the gas.

Furthermore, supply tube 18 constituting a supply path extends into operation portion 2 and insertion portion 14. The distal end of supply tube 18 is connected to a nozzle provided near the distal end of insertion portion 14. The nozzle is directed to spray cleaning water against an observation window.

Supply tube 18 is connected to air-/liquid-supply operation valve 5 inside control operation 3. End portions of water- and air-supply tubes 19 and 20 are respectively connected to operation valve 5. The other end portions of water- and air-supply tubes 19 and 20 are guided into universal cord 8, and connected to water and air sources (not shown), respectively. Water-supply tube 19 or air-supply tube 20 can be selectively caused to communicate with supply tube 18 by operating operation valve 5. When supply tube 18 is caused to communicate with water-supply tube 19 via operation valve 5, supply pipe path 21 for supplying cleaning water for cleaning the observation window is formed. Therefore, a water supply unit is constituted by operation valve 5 and supply pipe path 21.

Furthermore, connecting means 12 is provided on grip portion 4 of operation portion 2 so as to connect a supplementary injection unit such as a syringe for supplying supplementary air or water to supply tube 18.

Figure 3:
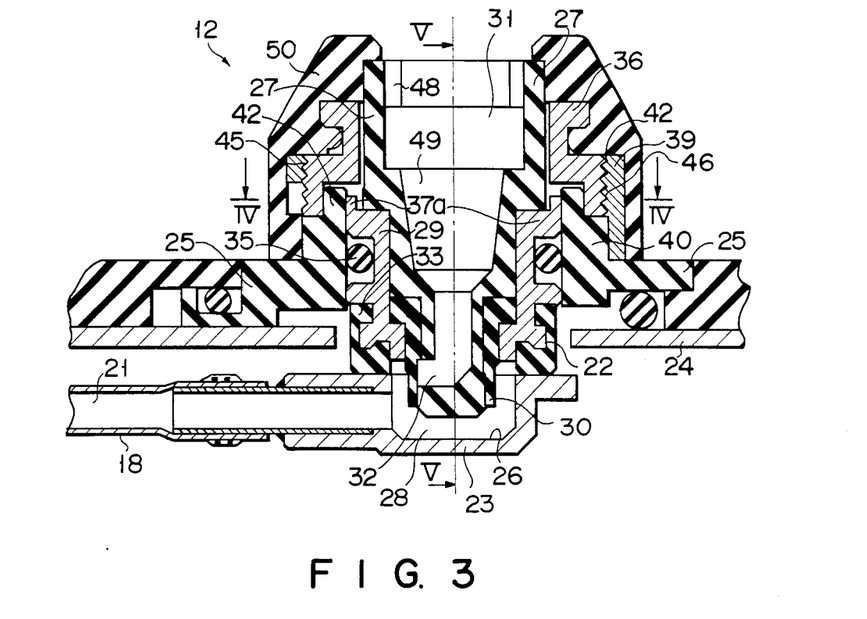
FIG. 3 is a schematic longitudinal sectional view of a connecting means arranged on the operation portion in FIG. 1.
Figure 4:
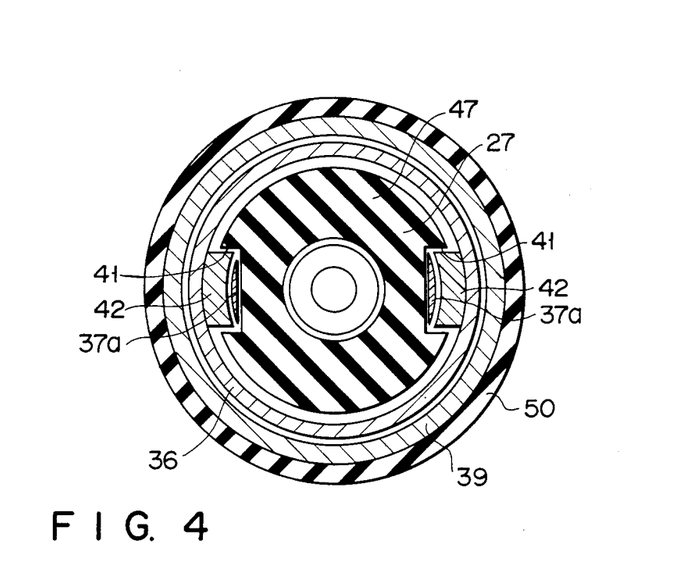
FIG. 4 is a sectional view taken along a line IV—IV in FIG. 3.
Figure 5:
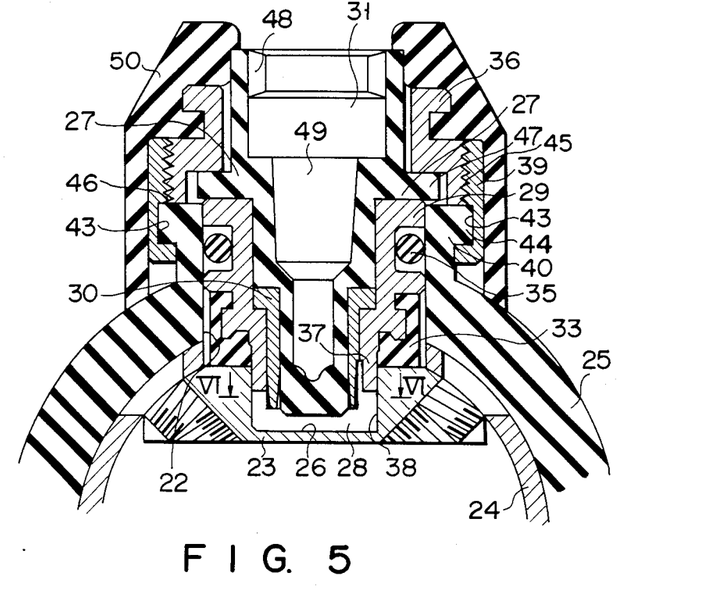
FIG. 5 is a sectional view taken along a line V—V in FIG. 3.

As shown in FIGS. 3 to 7, connecting means 12 includes block 23 disposed inside grip portion 4, and this block is inserted into a portion midway along supply tube 18. Block 23 can be fixed to main body 24 inside operation portion 2 using, e.g., as shown in FIG. 5, a thread or the like.

As shown in FIG. 5, substantially rectangular cavity 26 open on a side of cover 25 is formed on block 23. The distal end portion of mount piece 27 which is formed by an insulating material such as a synthetic resin to have a cylindrical shape with steps is inserted into cavity 26 through cover 25 and the opening portion of main body 24, thereby constituting sealed space 28 defined by mount piece 27 and supporting cylinder 29.

Furthermore, supporting cylinder 29 is fitted around mount piece 27, and sleeve 30 made of an elastic material is provided between mount piece 27 and supporting cylinder 29. Communicating hole 32 open in a transverse direction is formed on the distal end portion with a minimum diameter of mount piece 27, and is closed by sleeve 30. The minimum diameter portion and the sleeve constitute a check valve. Therefore, a liquid injected from opening portion 31 of mount piece 27 can flow from communicating hole 32 formed on the distal end to the inside of space 28 of cavity 26 through the gap formed between mount piece 27 and sleeve 30 by the liquid pressure. Sleeve 30 also serves as a seal member between mount piece 27 and supporting cylinder 29, as will be described later.

Seal member 33 is fitted in the lower portion of supporting cylinder 29 so as to seal the space between the upper portion of block 23 and supporting cylinder 29. Supporting cylinder 29 is water-tightly fitted in cover 25 by O-ring 35. In addition, supporting cylinder 29 is pressed from above by clamp ring 36 via mount piece 27. The pressing force compresses sleeve 30 to keep water-tight between supporting cylinder 29 and block 23, and compresses flange portion formed on sleeve 30 to keep water-tight between supporting cylinder 29 and mount piece 27. Projections 37a are formed on the upper end of supporting cylinder 29 to be fitted in notches 41 formed on mount piece 27 (refer to FIG. 4). Projections 37a circumferencially positions mount piece 27 so that looking piece 37, which will be described below, provided on the low end of supporting cylinder 29 may not disturb flow of fluid through hole 32 formed on lower end portion of mount piece.

Figure 6:
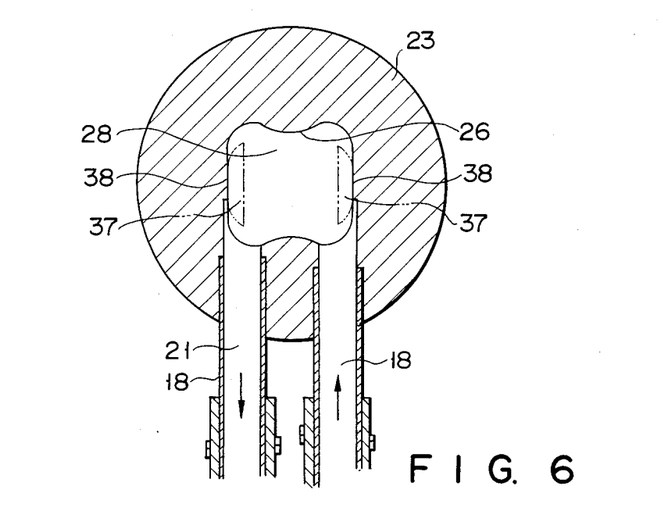
FIG. 6 is a sectional view taken along a line VI—VI in FIG. 5.

As shown in FIG. 5, a pair of locking pieces 37 are protruded from the lower end of supporting cylinder 29. Locking pieces 37 are in contact with side surface 38 of cavity 26 of block 23 as shown in FIG. 6 so as to prevent rotation of supporting cylinder 29 but to allow its movement in the axial direction in which supply tube 18 extends. Therefore, the area of the upper surface of block 23 which contacts seal member 33 is set to be larger than the positional error caused by a manufacturing tolerance between main body 24 of grip portion 4 and cover 25. Therefore, even if main body 24 is moved in relation to cover 25 due to the tolerance therebetween, the tolerance can be absorbed while the water-tight condition is kept.

A mounting structure of mount piece 27 and supporting cylinder 29 in relation to cover 25 will next be described.

Figure 7:
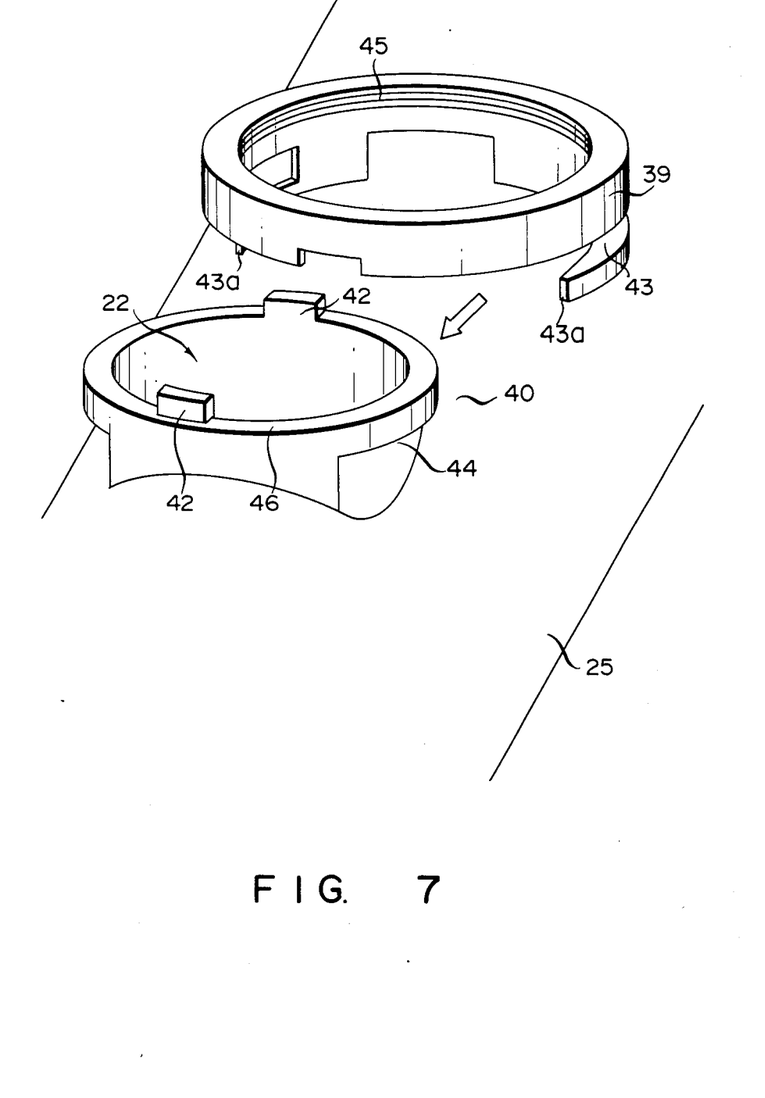
FIG. 7 is a schematic view illustrating a method of assembling a mount means of the connecting means in FIG. 3.

As shown in FIG. 7, cylindrical mount means 40 extends from the periphery portion of the opening 22 of the housing, i.e., cover 25. A pair of projections 42 are formed to extend from the upper end of mount means 40. Projections 42 are fitted in notches 41 formed on flange 47 of mount piece 27 as shown in FIGS. 3 and 4 so as to prevent mount piece 27 from rotating.

Shoulders 44 are formed near the upper end of mount means 40, and are fitted in fitting groove 43 formed on locking member 39. More specifically, when locking member 39 is slid sideway over shoulders 44 of mount means 40 and fitted in fitting groove 43 by, as shown in FIG. 7, arm 43a on the lower side constituting this fitting groove is brought into contact with the lower surfaces of shoulders 44, thereby preventing vertical movement of locking member 39. Note cover 25 and mount means 40 are integrally formed by an insulating material such as a plastic.

Female threaded portion 45 is formed on the inner surface of locking member 39, and clamp ring 36 constituting a support member is designed to be threadably engaged with threaded portion 45. The lower end portion of clamp ring 36 is formed to have two step of diameters larger than that of the upper portion. The lower end surface of the lower portion is brought into contact with upper end surface 46 of mount means 40 as shown in FIG. 5. The upper end portion of clamp ring 36 is formed to have a smaller diameter than that of flange 47 of mount piece 27 (FIGS. 4 and 5). Thus, when locking member 39 is mounted on mount means 40 of cover 25 and clamp ring 36 is threadably engaged with threaded portion 45 of the locking member, the stepped portion of clamp ring 36 is brought into contact with flange 47.

Threaded portion 48 for connecting a tube provided between mount piece 27 and the syringe used for supplying a supplementary liquid is formed on the inner surface of opening portion 31 of mount piece 27. Insulating cap 50 of an elastic material is mounted on the outer surfaces of clamp ring 36 and locking member 39 so as to insulate a metal portion exposed outwardly from cover 25.

Next, the assembly steps of connecting means 12 will be described below.

Locking member 39 is mounted sideway on mount means 40 formed on cover 25 as shown in FIG. 7. Then, supporting cylinder 29 with seal member 33 on its lower end and mount piece 27 with sleeve 30 on its distal end are inserted into the resultant structure. When clamp ring 36 is threadably engaged with threaded portion 45 of locking member 39, the lower end of locking member 39 is brought into contact with upper end surface 46 of mount means 40. When clamp ring 36 is further screwed into locking member 39, locking member 39 is pulled upwardly. Since shoulders 44 of mount means 40 are fitted in groove 43 of locking member 39, shoulders 44 and arm 43a are pulled toward each other with a great force due to clamp ring 36 which has been threadably engaged, thereby fixing locking member 39 and cover 25 to mount means 40.

Meanwhile, clamp ring 36 pushes flange portion 47 of mount piece 27 downwardly, and pushes seal member 33 against the upper surface of block 23. At the same time, clamp ring 36 causes sleeve 30 to be water-tightly clamped between supporting cylinder 29 and mount piece 27.

Figure 8:
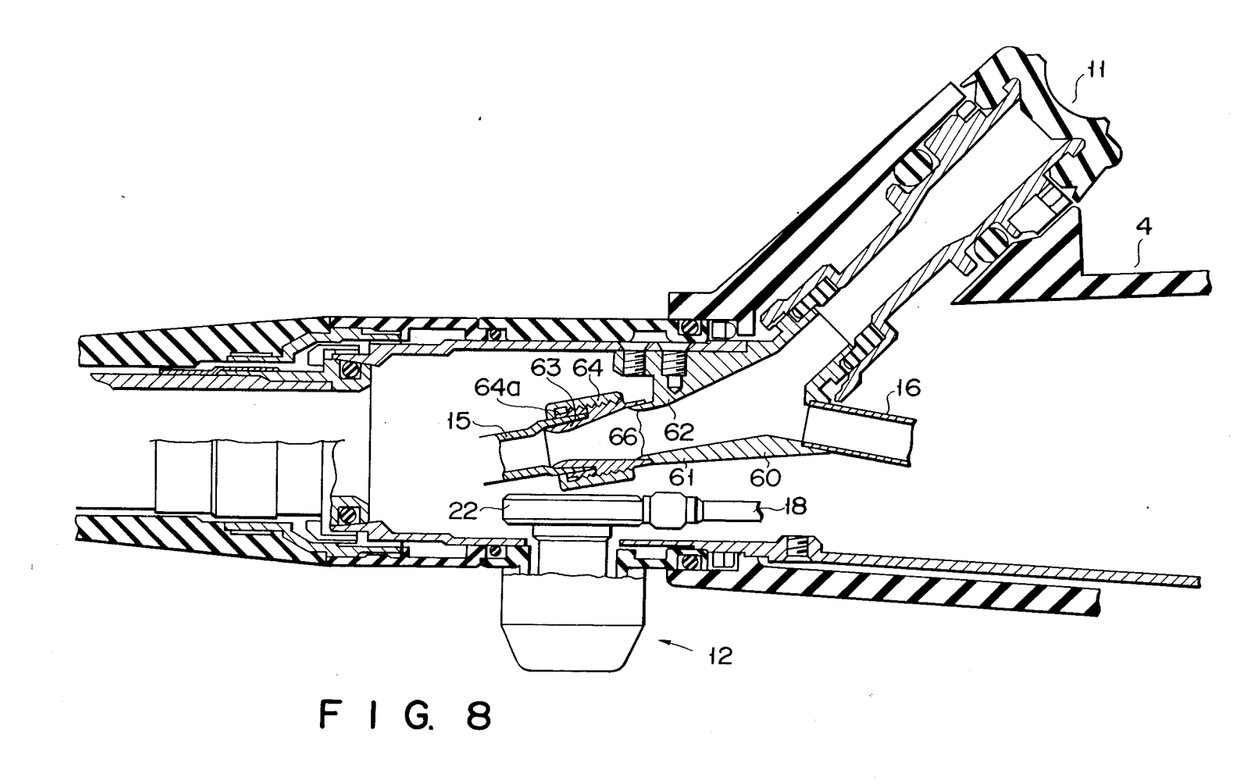
FIG. 8 is a schematic view illustrating a state wherein a treatment tool inserting tube is disposed together with the connecting means of the present invention.
Figure 9:
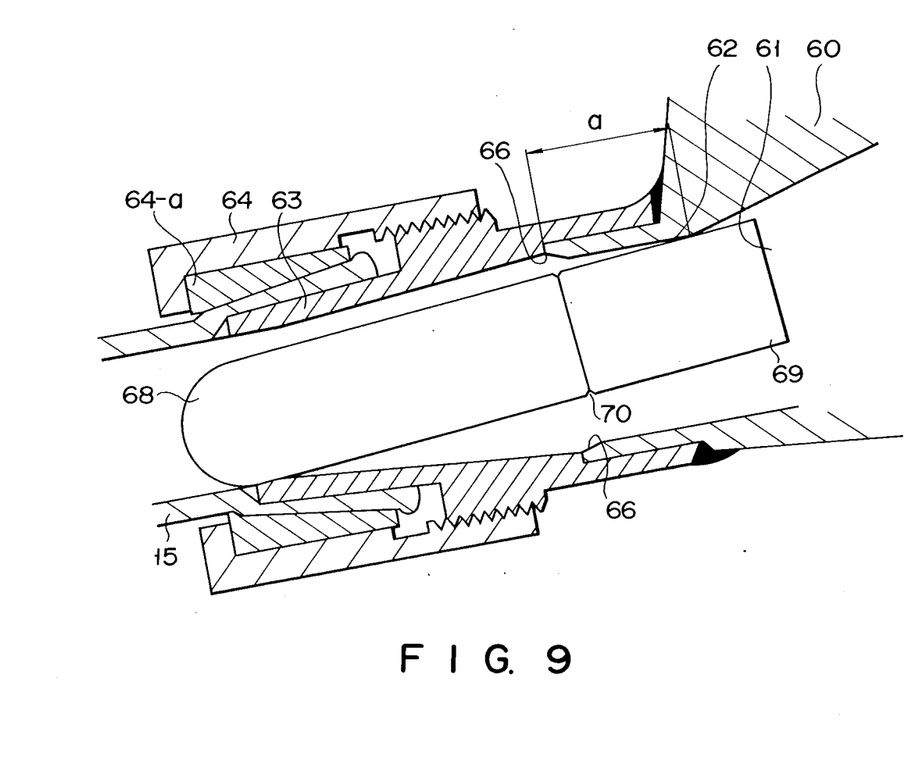
FIG. 9 is an enlarged view of a tube connecting portion in FIG. 8.

The structure of grip portion 4 on which connecting means 12 is arranged is shown in more detail in FIGS. 8 and 9.

Three-way connecting pipe 60 for connecting insertion portion 11, tube 15 for inserting a treatment tool, and suction tube 16 is formed on grip portion 4. Bent portion 62 is formed on the inner surface of branch pipe portion 61 to which tube 15 for inserting the treatment tool is connected by three-way connecting pipe 60. Bent portion 62 is arranged to be sufficiently separated from the distal end of branch pipe portion 61. In addition, one end of connecting pipe 63 whose inner surface is tapered is fitted in branch pipe portion 61. Tube 15 is fitted in the distal end of connecting pipe 63, and clamped and fixed by clamp ring 64 via tapered pipe 64a. Since bent portion 62 is sufficiently separated from the distal end of branch pipe portion 61 by a distance a as shown in FIG. 9, bent portion 62 is also sufficiently separated from connecting pipe 63. Furthermore, the distal end of branch pipe portion 61 is connected to the tapered surface of connecting pipe 63. Therefore, distal end portion 68 of treatment tool 67 to be inserted and step 70 between distal end portion 68 and sheath portion 69 are not likely to be caught by step 66 formed on the connecting portion of the distal end of branch pipe portion 61 and connecting pipe 63. In other words, there is little chance that they are scratched when the treatment tool is inserted and removed.

Thus, according to the present invention, the connecting means for connecting the supplementary injection means can be reliably and tightly fixed without using a metal material to form the external members of the operation portion. Since the external members of the operation portion can be made of an insulating material, electrical safety is assured when the endoscope is used. In addition, the external members of the operation portion can be formed by a material lighter in weight than the metal material, thereby realizing a lightweight operation portion. Disassembly of the supplementary injection unit can be easily performed, and hence damage caused upon disassembly of the unit can be minimized.

What is claimed is:

1. In an endoscope including an insertion portion to be inserted into a body cavity, the one end portion of which has an observation window and an orifice directed to face said observation window, an operation portion connected to the other end portion of said insertion portion, said operation portion having a housing formed with an opening, a supply path for supplying a fluid to said orifice, extending inside said insertion portion and said operation portion, and connecting means provided on said opening of said housing, for connecting fluid injection means for supplying a supplementary fluid into said fluid-supply path, the improvement in which said connecting means comprises:
a hollow mount member including shoulder means formed on the outer peripheral surface, and which is formed to extend from a periphery portion of said opening;
a block received in said housing, the block having a cavity facing said opening, and an inlet and outlet for enabling said cavity to be inserted serially in said supply path;
a mount piece which is inserted from the extended end of said mount member, such that its distal end portion is placed in said cavity, and on which a supplementary fluid injection means is detachably mounted;
a seal member for forming a seal between the mount piece and the periphery portion of said cavity;
a locking member having an arm abutting on the side of the shoulder means; and
a support member for supporting said mount piece, which is threadably fixed to said locking member to press said mount member, whereby said shoulder means is clamped between said support member and arm.

2. The endoscope according to claim 1, wherein said mount piece comprises a stepped hollow cylinder having a diameter increased incrementally from the distal end thereof, a communicating transverse hole formed in the distal end portion of the mount piece, and which includes a sleeve mounted on said distal end portion, so that the mount piece and sleeve together constitute a check valve.

3. The endoscope according to claim 2, which includes a supporting cylinder in which said mount piece and said sleeve are fitted, the supporting cylinder being sealed against the inner surface of said mount member and sealed against the opening surface of said block by said seal member.

4. The endoscope according to claim 3, wherein said supporting cylinder has a pair of locking pieces opposing each other on the inner end thereof, and said cavity is formed to have a rectangular cross section, so that said locking pieces are engaged with the side wall of said cavity, thereby to permit the block to move axially, relative to the housing, while preventing such movement in a circumferential direction thereof.

5. The endoscope according to claim 3, wherein said mount piece has a flange extending radially outward on an intermediate portion along the axial direction thereof, so that said flange is clamped between said supporting cylinder and said support member.

6. The endoscope according to claim 5, wherein said mount member has a pair of projections formed on the opposite positions of its outer end portion, said supporting cylinder has a pair of projections formed at positions matching with said projections at the outer end portion of said mount means, and said flange of said mount piece has a plurality of notches in which said projections of said mount means and said supporting cylinder can be respectively fitted.

7. The endoscope according to claim 1, wherein said housing is made of an insulating material, and includes an insulating cap for covering said locking member, said support member, and said mount piece.

8. The endoscope according to claim 6, wherein said housing is made of an insulating material, and includes an insulating cap for covering said locking member, said support member, and said mount piece.

* * * * *